United States Patent
Dong et al.

(10) Patent No.: US 10,383,978 B2
(45) Date of Patent: Aug. 20, 2019

(54) DRY ANIMAL-DERIVED COLLAGEN FIBER TISSUE MATERIAL AND PREPARATION METHOD AND BIOPROTHESIS THEREOF

(71) Applicant: SHANGHAI MICROPORT CARDIOFLOW MEDTECH CO., LTD., Shanghai (CN)

(72) Inventors: Jiaoming Dong, Shanghai (CN); Yemeng Chen, Shanghai (CN); Guanbiao Xu, Shanghai (CN); Xiulan Cheng, Shanghai (CN); Guoming Chen, Shanghai (CN); Yu Li, Shanghai (CN); Qiyi Luo, Shanghai (CN)

(73) Assignee: SHANGHAI MICROPORT CARDIOFLOW MEDTECH CO., LTD., Shanghai (CN)

( * ) Notice: Subject to any disclaimer, the term of this patent is extended or adjusted under 35 U.S.C. 154(b) by 0 days.

(21) Appl. No.: 15/571,953

(22) PCT Filed: May 4, 2016

(86) PCT No.: PCT/CN2016/080965
§ 371 (c)(1),
(2) Date: Nov. 6, 2017

(87) PCT Pub. No.: WO2016/180259
PCT Pub. Date: Nov. 17, 2016

(65) Prior Publication Data
US 2018/0133365 A1 May 17, 2018

(30) Foreign Application Priority Data
May 8, 2015 (CN) .......................... 2015 1 0232587

(51) Int. Cl.
| | |
|---|---|
| A61L 27/36 | (2006.01) |
| A61L 27/24 | (2006.01) |
| A61L 27/60 | (2006.01) |
| A61L 27/58 | (2006.01) |

(52) U.S. Cl.
CPC ........... *A61L 27/3687* (2013.01); *A61L 27/24* (2013.01); *A61L 27/3604* (2013.01); *A61L 27/3625* (2013.01); *A61L 27/3629* (2013.01); *A61L 27/3691* (2013.01); *A61L 27/58* (2013.01); *A61L 27/60* (2013.01)

(58) Field of Classification Search
CPC ...................................................... A61L 27/24
See application file for complete search history.

(56) References Cited

U.S. PATENT DOCUMENTS

| | | |
|---|---|---|
| 2001/0023372 A1 | 9/2001 | Chen et al. |
| 2008/0102439 A1 | 5/2008 | Tian et al. |
| 2015/0064228 A1 | 3/2015 | Iwasaki et al. |

FOREIGN PATENT DOCUMENTS

| | | |
|---|---|---|
| CN | 1306445 A | 8/2001 |
| CN | 101128225 A | 2/2008 |
| CN | 101965205 A | 2/2011 |
| CN | 102438445 A | 5/2012 |
| CN | 103933612 A | 7/2014 |
| WO | WO 1999066967 | 12/1999 |
| WO | WO 2013147299 A1 | 10/2013 |
| WO | WO 2014019672 A1 | 2/2014 |

OTHER PUBLICATIONS

Lim et al. European J of Cardio-Thoracic Surgery, 2014, 41:383-390.*
Yu, et al. J of Biomedical Optics, 2011, 16:1-9.*
Masoud Mirzaie, et al., "A New Storage Solution for Porcine Aortic Valves", Ann Thorac Cardiovasc Surg, 2007, pp. 102-109, vol. 13, No. 2.

* cited by examiner

*Primary Examiner* — Bin Shen
(74) *Attorney, Agent, or Firm* — Muncy, Geissler, Olds & Lowe, P.C.

(57) ABSTRACT

A dry animal-derived collagen fiber tissue material and preparation method and bioprosthesis thereof are disclosed. The preparation method includes: 1) rinsing of an animal-derived collagen fiber tissue material that has been treated with a crosslinking agent; 2) immersion of the rinsed tissue material in a non-aqueous alcoholic solution for dehydration; 3) successive immersion of the tissue material that has been dehydrated with the non-aqueous alcoholic solution in saccharide solutions of different gradients of concentrations for gradient dehydration; 4) taking out and drying of the gradient dehydrated tissue material; and 5) hermetic packaging of the dried tissue material and sterilization. The preparation method is simple and allows the use of easily-available low-cost materials, resulting in lower costs. In addition, it can reduce the toxicity caused by a residue of the aldehyde crosslinking agent. The prepared biological tissue material is pliable and tough, less prone to bending or warping, has a water content that can be well controlled and better biocompatibility due to absence of polyhydric alcohol residues.

18 Claims, 4 Drawing Sheets

DRY ANIMAL-DERIVED COLLAGEN FIBER TISSUE MATERIAL AND PREPARATION METHOD AND BIOPROTHESIS THEREOF

The present application is a national stage of, and claims priority to, PCT/CN2016/080965 filed on May 5, 2016, which claims priority to Chinese Patent Application No. 201510232587.3 filed on May 8, 2015. The disclosures of these applications are hereby incorporated by reference in their entirety.

TECHNICAL FIELD

The present invention relates to the field of medical biomaterials and, more particularly, to a dry animal-derived collagen fiber tissue material and preparation method and bioprosthesis thereof.

BACKGROUND

Animal-derived collagen fiber tissue materials commonly used in the current clinical practice, such as bioprosthetic biovalve, transcatheter aortic valves and biological patches like bovine pericardium, small intestinal submucosa, etc., are usually preserved with chemical reagents such as glutaraldehyde and/or formaldehyde, or treated with such chemical reagents for crosslinking. And tissues are placed in dilute aqueous solutions containing glutaraldehyde and/or formaldehyde so that the components of the tissues are kept in a sterile environment and hence maintain their hydrated state typically. However, extensive studies have shown that glutaraldehyde remaining in implanted prostheticbiovalve can promote the calcification of the biovalve. Absence of aldehydes during the preservation can lead to significantly slower calcification of the biovalve. Mirzaie et al. preserved a porcine bioprosthetic aortic valve in a solution based on human serum solution in lieu of a glutaraldehyde solution and confirmed a reduction of about 50% of calcium in the valve. In addition, glutaraldehyde has a high toxicity, and even a very small glutaraldehyde residue may have a poisoning effect on the human body and affect the formation of endothelium (more details in this regard can be found in Mirzaie M, Brunner E, Mahbub-ul Latif A H, et al. A new storage solution for porcine aortic valves. Ann Thorac Cardiovasc Surg, 2007, 13:102-109). So, bioprosthetic tissues treated or preserved with glutaraldehyde must be rinsed many times in order to remove glutaraldehyde before the implantation. Further, as exposure to the aldehydes contained in such preservative solutions may cause a significant harm to health, additional protective measures are necessary for the production workers, medical personnel and patients, leading to increased costs and inconvenience. It is conceivable that reducing medical staff's preparatory efforts as much as possible prior to the implantation of biological tissue materials and prostheses prepared therefrom by providing them in a form ready for use can reduce not only the chance for infections or faults but also the time required for the implantation. Thus, development of novel methods for dry state preservation of biological tissues is promised with good prospects and is of high application value.

Presently, biological tissues are often preserved in a lyophilized form by converting water in the tissues into ice crystals at −80° C. and then freeze-drying them at reduced pressures (vacuum drying) to obtain the dry tissues. However, such lyophilized biological tissues are not tough and prone to breaks or fractures due to a lack of moisture and hydrophilic solvents, and their production cost is relatively high. Moreover, the formation of ice crystals may lead to structural damage to the tissues, and it is difficult for the dry biological tissues to be rehydrated and it takes a few days to recover their original hydrated state.

Chinese Patent Pub. No. CN1306445A describes a method for treating a tissue with a solvent. The method involves treating the biological tissue with an increasing gradient of concentration of a polar organic solvent (selected from methanol, ethanol, isopropanol, acetonitrile, acetone and butanone) and then treating the biological tissue with a solution containing glycerol or low molecular weight (<1000 D) polyethylene glycol, and polyethylene glycol of a molecular weight between 6,000 D to 15,000 D and heparin. After that, the biological tissue is immersed in an aqueous heparin solution shortly, frozen and lyophilized. However, this dehydration process significantly reduces the overall size of the tissue and the chemical reagents used (e.g., acetonitrile, acetone, etc.) is toxic. Additionally, the biological tissue obtained from this dehydration process cannot be rehydrated and recovered to its original size.

Fumoto et al. reported absence of significant deterioration in size, shape or in vitro pulsed flow performance of a tissue after it was subjected to treatment with a 57% aqueous glycerol solution, drying in an environment with a relative humidity of less than 28% for 6 to 8 hours and sterilization with ethylene oxide (EO). Reference can be made to Fumoto H, Chen J F, Zhou Q, et al. Performance of bioprosthetic valves after glycerol dehydration, ethylene oxide sterilization, and rehydration. Innovations (Phila), 2011, 6(1): 32-36 for more details in this regard.

Chinese Patent Pub. No. CN101965205A describes a method for preparing a biological tissue or prosthesis by dehydration and drying with a glycerol/ethanol (75%/25%) mixture.

Chinese Patent Pub. No. CN103933612A relates to a biological tissue for surgical implantation. The biological tissue is treated with a non-aqueous solution including a polyhydric alcohol (selected from glycerol, propylene glycol, glycerol derivatives, propylene glycol derivatives and mixtures thereof) and a $C_1$-$C_3$ alcohol (selected from methanol, ethanol, isopropanol and n-propanol), and a portion of the solution is removed from the solution-treated biological tissue. This method can maintain the tissue in a substantially dry state. However, the treated tissue tends to bend or warp subsequent to the partial removal of the treatment solution and contains residues of the treating agents which are hard to be removed and may affect the sterilization process. In addition, treatment simply with the alcohols fails to allow effective control of the remaining water content of the treated tissue in the "substantially dry" (a water content greater than 30% will affect the sterilization performance of EO and lead to insufficient sterilization).

To sum up, the existing biological tissue preservation methods, such as those using aldehyde solutions or lyophilization as mentioned above, have a number of disadvantages such as toxicity of the residual reagents, morphological deformation of the tissue and high cost and thus need modifications and improvements in terms of application. While the glycerol-based non-hydrophilic dehydration methods to dry animal-derived collagen fiber tissue are relatively advantageous, they still need further improvements in morphological deformation of the biological tissue, residues of the reagents and water content variations.

SUMMARY OF THE INVENTION

It is therefore an objective of the present invention to provide a dry animal-derived collagen fiber tissue material which has good flexibility, no reagent residues and a water content controllable within the range of from 10% to 25% which is conducive to subsequent sterilization.

To this end, in a first aspect of the present invention, a preparation method of a dry animal-derived collagen fiber tissue material is provided, including: 1) rinsing of an animal-derived collagen fiber tissue material that has been treated with a crosslinking agent; 2) immersion of the rinsed tissue material in a non-aqueous alcoholic solution for dehydration; 3) successive immersion of the tissue material that has been dehydrated with the non-aqueous alcoholic solution in saccharide solutions of different gradients of concentrations for gradient dehydration; 4) taking out and drying of the gradient dehydrated tissue material; and 5) hermetic packaging and sterilization of the dried tissue material.

Additionally, the animal-derived collagen fiber tissue material in step 1) may be a biological tissue obtained from animals of different species or different animals of a same species.

Additionally, the biological tissue material may be pericardium, heart valves, peritoneum, pleura, small intestinal submucosa, dura mater, spinal dura, ligaments or skin.

Additionally, the crosslinking agent in step 1) may be one or more of glutaraldehyde, genipin, procyanidins and carbodiimide.

Additionally, the rinsing in step 1) may be accomplished by shaking at 50-150 rpm for 3-60 minutes at 4-25° C. in an isotonic solution containing 5%-30% (v/v) of isopropanol and/or ethanol.

Additionally, the isotonic solution may be a normal saline solution, or a phosphate buffer solution having a pH of 6.8-8.6, or a D-Hanks buffer solution having a pH of 6.8-8.6.

Additionally, the non-aqueous alcoholic solution in step 2) may be a solution of aliphatic alcohol(s) with each aliphatic alcohol having a molecular weight of less than 1000 D.

Additionally, the non-aqueous alcoholic solution may be a solution of a polyether diol or a $C_2$-$C_6$ aliphatic alcohol.

Additionally, the non-aqueous alcoholic solution may be a solution of one or more of polyethylene glycol, triethylene glycol, 1,2,6-hexanetriol, 1,2,4-butanetriol, 1,3-butanediol, 1,4-butanediol, 1,5-pentanediol, glycerol, isopropanol and ethanol.

Additionally, the non-aqueous alcoholic solution may contain polyethylene glycol or glycerol accounting for 20%-90% by volume or contain polyethylene glycol and glycerol together accounting for 20%-90% by volume.

Additionally, the polyethylene glycol may have a number-average molecular weight of 200-1000.

Additionally, in step 2), the non-aqueous alcoholic solution may be kept at 20-37° C., and the tissue material may be immersed for 30 minutes to 24 hours in a dark condition.

Additionally, each of the saccharide solutions in step 3) may be a solution of a moisturizing monosaccharide, disaccharide, trisaccharide, polysaccharide or sugar alcohol that can absorb moisture.

Additionally, each of the saccharide solutions may be a solution of fructose, saccharose, trehalose, non-crystalline raffinose, chitosan, a chitosan-modified polysaccharide, sorbitol or mannitol.

Additionally, the gradient dehydration in step 3) may be accomplished by immersing the tissue material that has been dehydrated with the non-aqueous alcoholic solution successively in each of the saccharide solutions of different gradients of concentrations at 4-37° C. in a dark condition for 5 minutes to 48 hours.

Additionally, the saccharide solutions of different gradients of concentrations in step 3) may be respectively 30%, 40%, 50%, 55%, 60% and 65% (w/v) aqueous saccharose solutions or 50%, 60%, 70%, 75%, 80% and 85% (w/v) aqueous solutions of fructose, trehalose, non-crystalline raffinose, chitosan, chitosan-modified polysaccharide, sorbitol or mannitol.

Additionally, in step 4), the gradient dehydrated tissue material may be taken out and dried by using a fibrous desiccant or by placing the gradient dehydrated tissue material in a dark condition at 20° C. to 37° C. for 10 minutes to 24 hours.

Additionally, the fibrous desiccant may be provided in a form of raw sheets, folded sheets, sheets in bags, columns and lamination.

Additionally, the hermetic packaging may be accomplished by hermetically sealing the dried tissue material in a packaging container in an environment with a relative humidity of less than 30% or in an inert environment.

Additionally, the sterilization may be accomplished by ethylene oxide, electron beam irradiation or gamma ray irradiation.

In another aspect of the present invention, a dry animal-derived collagen fiber tissue material prepared by the preparation method as defined above is provided.

In a third aspect of the present invention, a bioprosthesis made from the dry animal-derived collagen fiber tissue material as defined above is provided.

The present invention has the advantages over the prior art as follows: 1) as the method is simple and allows the use of easily-available low-cost materials, it is suitable for mass production which can result in lower medical costs; 2) rinsing of the cross-linked biological tissue with the isotonic solution containing isopropanol or ethanol can preliminarily remove the crosslinking agent (e.g., glutaraldehyde and formaldehyde) remaining in the tissue, thus reducing the toxicity caused by a residue of the crosslinking agent; 3) the biological tissue material treated with the combination of physical drying such as the fibrous desiccant and chemical drying which including the dehydration by the non-aqueous alcoholic solution and the hyperosmotic dehydration by the saccharide solution of different gradients of concentration is pliable and tough, less prone to bending or warping, has a water content that can be well controlled and better biocompatibility due to absence of polyhydric alcohol residues; 4) the saccharide with the hyperosmotic dehydration (especially saccharose) enables higher biological safety and lowers calcification potential of the biological tissue, because it can not only absorb moisture from the biological tissue but can further remove the crosslinking agent remaining therein (e.g., glutaraldehyde and formaldehyde). And the saccharide with the hyperosmotic dehydration provides, together with the gradient dehydration approach, strong protection for the composition and structure of the tissue because it can penetrate into the tissue to prevent the formation of voids or breaks therein due to rapid loss of water; 5) drying the biological tissue in a dark condition helps it maintain the original composition and structure and prevents the dry tissue from being oxidized or structurally damaged; and 6) the prepared biological tissue material and prosthesis made therefrom are highly biocompatible, flexible, tough and excellent in mechanical properties, allow safe and reliable use and easy clinical operation. And they can be rehydrated rapidly in a normal saline solution (usually, it can recover the original hydrated state in about 5 minutes), and have other advantages.

DETAILED DESCRIPTION

The present invention will be described in further detail below with reference to embodiment examples and the accompanying drawings.

Figure 1:
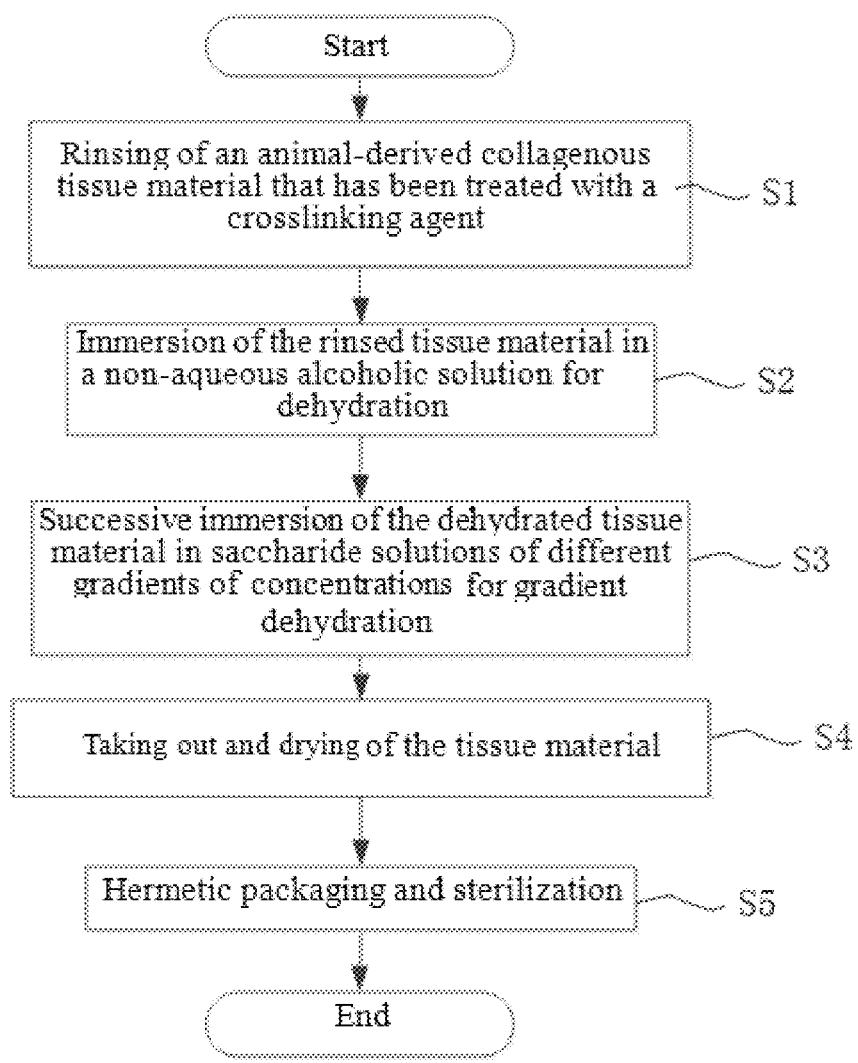
FIG. 1 is a flow chart of a method for preparing a dry animal-derived collagen fiber tissue material in accordance with embodiments of the present invention.

With reference to FIG. 1, a method for preparing a dry animal-derived collagen fiber tissue material according to the present invention includes the steps detailed below.

In S1, an animal-derived collagen fiber tissue material that has been treated with a crosslinking agent is rinsed.

According to the present invention, the animal-derived collagen fiber tissue material that has been treated with the crosslinking agent is a biological tissue material derived from tissues of animals of different species or different animals of the same species, such as pericardium, heart valves, peritoneum, pleura, small intestinal submucosa, dura mater, spinal dura, ligaments and skin.

The present invention is not limited to any particular crosslinking agent for treating the animal-derived collagen fiber tissue material and, as an example, any of the commonly used glutaraldehyde, genipin, procyanidins, carbodiimide and other new crosslinking agents and mixtures thereof is suitable.

The present invention is not limited to any particular method for treating the animal-derived collagen fiber tissue material by the crosslinking agent and, as an example, either of chemical leaching and vapor treatment is suitable.

The present invention is not limited to any particular concentration of the crosslinking agent for treating the animal-derived collagen fiber tissue material.

Preferably, the term "rinsing" refers to rinsing by shaking at 50-150 rpm for 3-60 minutes at 4-25° C. in an isotonic solution containing 5%-30% (v/v) of isopropanol and/or ethanol. Here, the isotonic solution containing 5%-30% (v/v) of isopropanol and/or ethanol is an isotonic solution containing 5%-30% (v/v) of isopropanol, or an isotonic solution containing 5%-30% (v/v) of ethanol, or an isotonic solution containing 5%-30% (v/v) of isopropanol and ethanol that are added at any ratio.

The isotonic solution is a normal saline solution, or a phosphate buffer solution having a pH of 6.8-8.6, or a D-Hanks solution having a pH of 6.8-8.6 (e.g., a calcium-free Hanks containing magnesium ions, Gibco).

In S2, the rinsed tissue material is immersed in a non-aqueous alcoholic solution (not containing moisture) for dehydration.

According to the present invention, the non-aqueous alcoholic solution is a solution of low molecular weight (<1000 D) aliphatic alcohol(s), with polyether diol(s) (of the formula OH—(R—O—)$_n$—R—OH, where R is an alkylidene group, preferably a $C_2$-$C_6$ alkylidene group) and/or $C_2$-$C_6$ aliphatic alcohol(s) (e.g., $C_2$-$C_6$ monohydric alcohol(s), $C_2$-$C_6$ diols(s), $C_2$-$C_6$ triol(s) and $C_2$-$C_6$ tetrahydric alcohol(s)) being preferred, and with one or more of polyethylene glycol, triethylene glycol, 1,2,6-hexanetriol, 1,2,4-butanetriol, 1,3-butanediol, 1,4-butanediol, 1,5-pentanediol, glycerol, isopropanol and ethanol being more preferred.

The polyethylene glycol may have a number-average molecular weight of 200-1000. For example, the polyethylene glycol is one or more of polyethylene glycol 200, polyethylene glycol 300, polyethylene glycol 400, polyethylene glycol 600, polyethylene glycol 800 and polyethylene glycol 1000.

In case the non-aqueous alcoholic solution is a mixture, the amounts of its components are not particularly limited. Preferably, the mixture has two components each accounting for 5-95% by volume of the mixture, or three components each accounting for 5-90% by volume of the mixture, or four components each accounting for 5-85% by volume of the mixture, or five components each accounting for 5-80% by volume of the mixture. More preferably, the components of the mixture include polyethylene glycol or glycerol accounting for 20-90% by volume of the mixture. Preferably, the components of the mixture include polyethylene glycol and glycerol, which together account for 20-90% by volume of the mixture and are added at an arbitrary ratio.

According to the present invention, the tissue material may be immersed in the non-aqueous alcoholic solution at 20-37° C. for 30 minutes to 24 hours, preferably 1 hour to 12 hours, in a dark condition.

In S3, the tissue material treated with the treatment in S2 is successively immersed in saccharide solutions of different gradients of concentrations.

According to the present invention, the saccharide may be a monosaccharide, disaccharide, trisaccharide, polysaccharide, sugar alcohol or similar moisturizing low molecular weight saccharide that can absorb moisture, such as, for example, fructose, saccharose, trehalose, raffinose (non-crystalline), chitosan, chitosan-modified polysaccharides, sorbitol or mannitol.

According to the present invention, successively immersing the tissue material in saccharide solutions of different gradients of concentrations refers to subjecting the tissue material to gradient dehydration in which each of the aqueous saccharide solutions of different concentrations is kept at 4-37° C., and the tissue material is immersed therein for 5 minutes to 48 hours, preferably 30 minutes to 24 hours, more preferably 1 hour to 12 hours in a dark condition. In some embodiments, the aqueous saccharide solutions of different gradients of concentrations are aqueous saccharose solutions having concentrations of 30%, 40%, 50%, 55%, 60% and 65% (w/v). In some other embodiments, the aqueous saccharide solutions of different gradients of concentrations are aqueous solutions of fructose, trehalose, non-crystalline raffinose, chitosan, chitosan-modified polysaccharide, sorbitol or mannitol that have concentrations of 50%, 60%, 70%, 75%, 80% and 85% (w/v).

In S4, the tissue material is dried in a clean and dry environment and/or dried with a fibrous desiccant.

The present invention is not limited to any particular fibrous desiccant, and preferably the fibrous desiccant may be provided in a form selected from raw sheets, folded sheets, sheets in bags, columns and lamination, with lamination being more preferred.

According to the present invention, preferably the dry and clean environment may be a Class 10,000 or 100 cleanrooms with humidity less than 20%. In the clean environment, the tissue material may be dried at 20° C. to 37° C. in a dark condition for 10 minutes to 24 hours, preferably 1 hour to 8 hours. The present invention is not limited to any particular method for creating the clean environment, and it may be created by reducing moisture in the air or by ventilation with dry air.

In S5, hermetic packaging and sterilization are carried out successively.

According to the present invention, preferably the hermetic packaging may be a process involving hermetically packaging the tissue material and/or a bioprosthesis thereof into a liquid-free bag or other container in an environment with a relative humidity of less than 30% or in a nitrogen, argon or other inert environment.

According to the present invention, preferably the sterilization may be accomplished by ethylene oxide (EO), electron beam irradiation or gamma ray irradiation.

Test Methods

The following criteria and test methods were adopted to evaluate each of dry animal-derived collagen fiber tissue materials prepared in accordance with the present invention.

1. Rat subcutaneous implantation and pathological observation: male juvenile Wistar rats were anaesthetized, and 15 mm×15 mm sample pieces of the tissue material were implanted therein through incisions on their backs made under an aseptic condition. The rats were maintained for 28 days, and after the 28 days, the rats were killed with carbon dioxide. The tissue sample pieces were retrieved, fixed with a 10% neutral formalin solution, embedded in paraffin and cut into 0.4 micron thick slices which were, in turn, dewaxed with dimethylbenzene, dehydrated with a series of ethanol solutions, stained with hematoxylin-eosin (HE) and observed for fibers and inflammation.

2. Water content of the tissue material: a wet sample was sandwiched between two pieces of dry filter paper, and a mass weighing 50 grams was placed on the filter paper for 30 seconds. The wet weight of the sample was then measured. The sample was lyophilized for 24 hour and its dry weight was measured. The water content of the sample was determined according to: water content=(wet weight−dry weight)/dry weight×100%.

3. Surface morphology of the tissue material: the tissue material was cross-linked with a 2.5% glutaraldehyde solution, subjected to an increasing gradient of concentration of ethanol for dehydration, dried, vacuum-coated with gold and observed by a scanning electron microscope (SEM) for its surface morphology and fiber arrangement.

4. Tensile strength of the tissue material: the tissue material was cut into plates which were then tested on a universal material tester. The tensile strength of the tissue material was calculated by dividing the maximum tensile force by the material's cross-sectional area to indicate its resistance to tension.

5. Rehydration time of the tissue material: a 15 mm×15 mm sample piece of the tissue material was immersed in a normal saline solution at 37° C. and taken out at different time points for determination of its water contents according to the method described in the above "2. water content of the tissue material". The time point when the water content of the tissue material reached 70% was recorded.

6. Shrinkage temperature of the tissue material: six 50 mm×3 mm strip-like samples were cut from the tissue material and tested on a leather shrinkage temperature tester with distilled water as a medium, in order to measure the shrinkage temperatures.

7. In vitro cytotoxicity of the tissue material: cytotoxicity of the tissue material was measured using the leaching and MTT assays defined in the GB16886.5-2003 and GB/T 14233.2-2005_8 standards.

Example 1

Bovine pericardium was harvested from an abattoir, subjected to fat separation, trimming and cleaning, then cross-linked with a 0.625% (v/v) glutaraldehyde (Sigma-Aldrich Co. LLC.) solution for more than three days to obtain glutaraldehyde cross-linked bovine pericardium. The obtained bovine pericardium was cut into small pieces (15 mm×15 mm) which were then rinsed by shaking at 100 rpm in a normal saline solution (Shandong Kangning Pharmaceutical Co., Ltd., batch number: A14100807) containing 10% (v/v) of isopropanol (Sinopharm Chemical Reagent Co., Ltd) at 20° C. for 3-5 times, 3-5 minutes each time. Afterward, the bovine pericardium pieces were immersed at 20° C. for 4 hours in an alcoholic solution that containing 70% (v/v) of polyethylene glycol 200 (Shanghai Jingchun Biochemical Technology Co., Ltd.) and 30% (v/v) of 1,3-butanediol (Sigma-Aldrich Co. LLC) that was held in a blue-cover reagent bottle completely wrapped with tin foil. Then the bovine pericardium pieces were immersed successively in each of 30%, 40%, 50%, 55%, 60% and 65% (w/v) aqueous saccharose (Shanghai Jingchun Biochemical Technology Co., Ltd.) solutions at 20° C. for 30 minutes, each of which was held in a blue-cover reagent bottle completely wrapped with tin foil. Subsequently, in a dry clean environment, the bovine pericardium pieces were taken out and dried on fibrous desiccant lamination (Shanghai Hengyuan Macromolecular Materials Co., Ltd.). Finally, in a dry and clean environment, the dry bovine pericardium pieces were hermetically packaged in dialysis bags (Tyvek®, DuPont China Group Co., Ltd.) and sterilized with EO.

Figure 2:
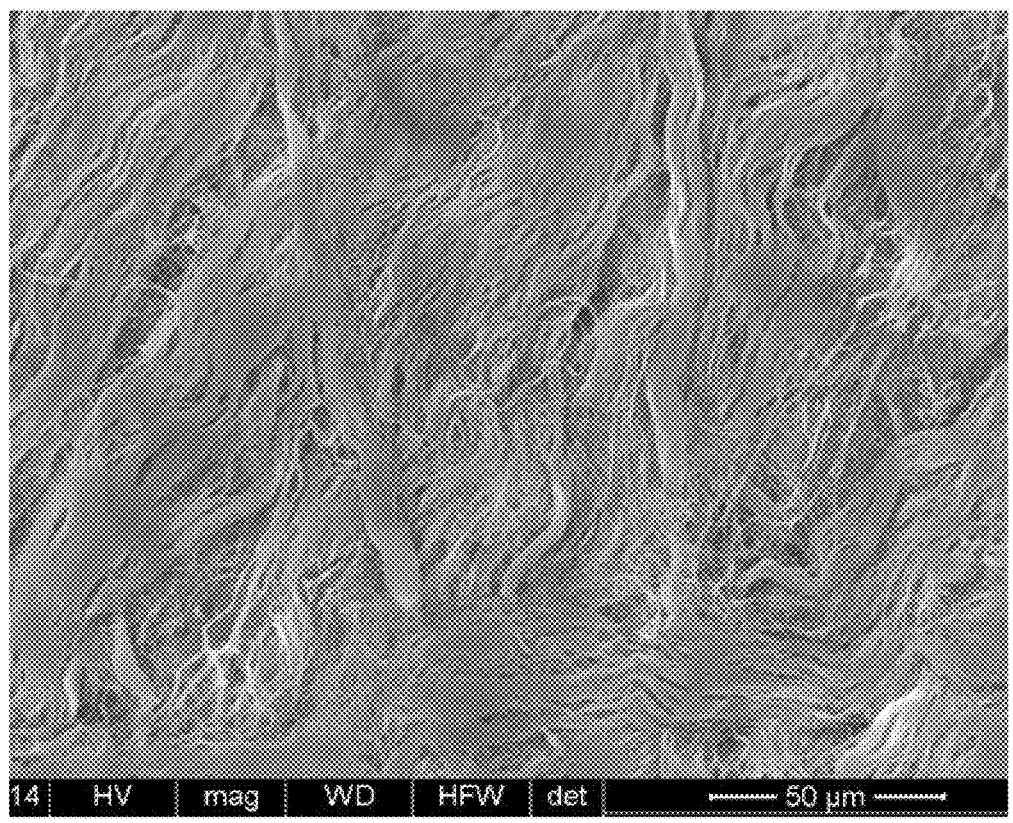
FIG. 2 shows a scanning electron microscope (SEM) image (1200×) of a dry bovine pericardium sample.
Figure 3:
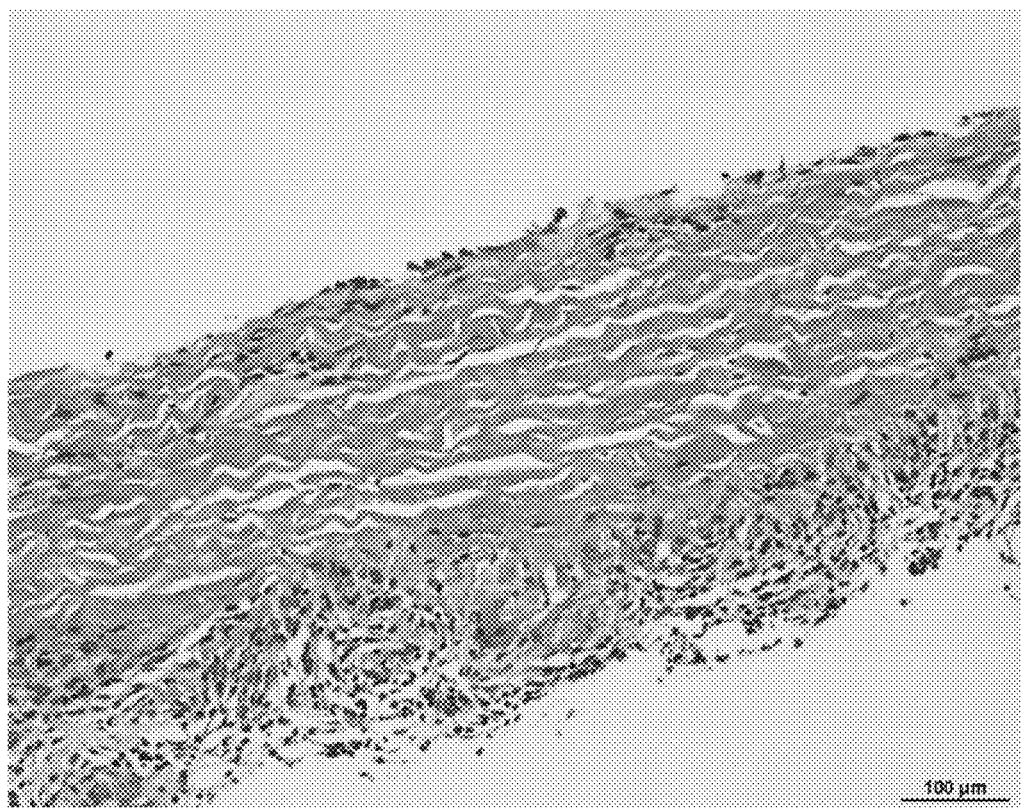
FIG. 3 is an image of an undried control bovine pericardium sample that has been subcutaneous implanted in a Wistar rat for 4 weeks and stained with hematoxylin-eosin (HE) in accordance with a first embodiment example of the present invention.
Figure 4:
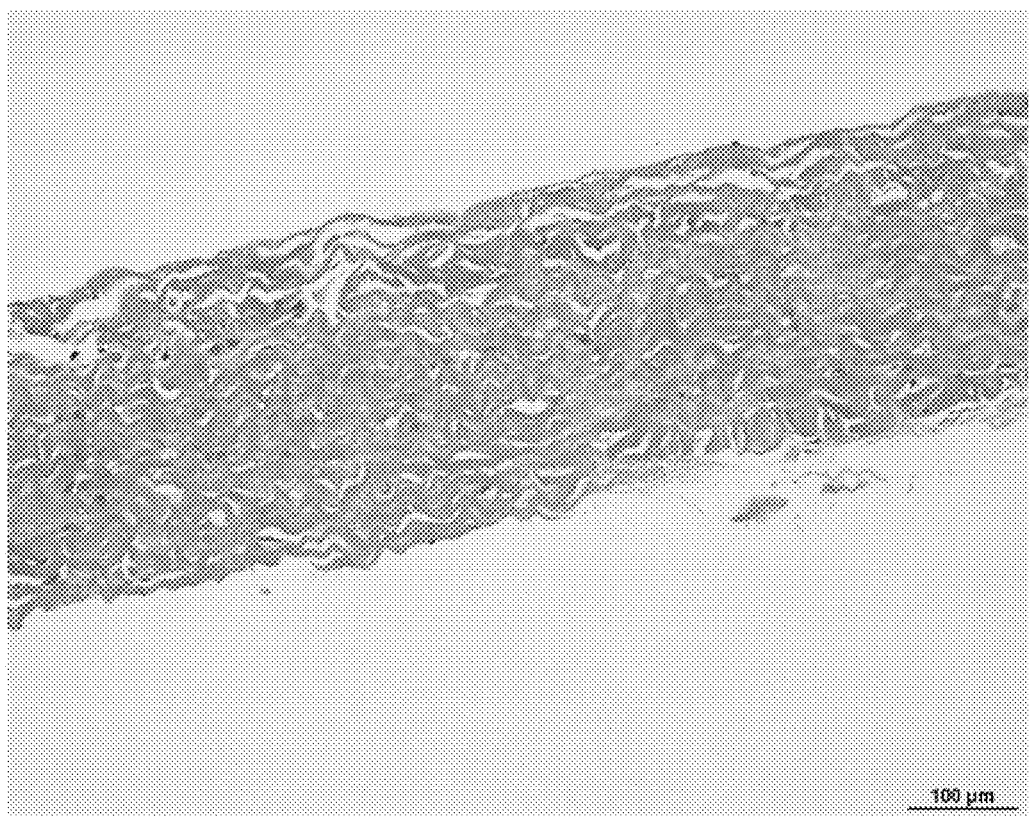
FIG. 4 is an image of a prepared dry bovine pericardium sample that has been subcutaneous implanted in a Wistar rat for 4 weeks and stained with HE in accordance with the first embodiment example of the present invention.

FIG. 2 shows a scanning electron microscope (SEM) image of the dry bovine pericardium. As can be seen from FIG. 2, collagen fibers in the bovine pericardium dried in accordance with the present invention were continuous without significant breaks, wavy and arranged neatly and compactly. The prepared dry bovine pericardium had a water content of 17.3±1.8%, a rehydration time of 5.37±0.42 minutes, a shrinkage temperature of 86.67±1.35° C., a Class I cytotoxicity and a maximum tensile strength of 12.5±6.6 N. By subcutaneously implanting an untreated bovine pericardium and the sterilized dry bovine pericardium in a Wistar rat for 4 weeks, we could find that: an image of the untreated bovine pericardium sample that had been subcutaneously implanted in a Wistar rat for 4 weeks and stained with hematoxylin-eosin (HE) showed that while fibers therein were continuous, wavy and substantially oriented in the same direction, inflammatory cells scattered therethrough and newborn capillaries and significant inflammatory cell infiltration in a loose connective tissue portion along one edge thereof were observed (see FIG. 3). In contrast, an image of the dry bovine pericardium that had been subcutaneously implanted in a Wistar rat for 4 weeks and stained with HE showed that, fibers therein were continuous, wavy and substantially oriented in the same direction, and no inflammatory cells, inflammatory cell infiltration or calcification sites were observed (see FIG. 4). Therefore, the bovine pericardium prepared in accordance with the present invention had excellent biocompatibility and could maintain the original tissue structure and state.

Example 2

A porcine aortic valve was harvested from an abattoir, cleaned and cross-linked with a 0.625% (v/v) glutaraldehyde solution for more than three days to obtain glutaraldehyde cross-linked porcine aortic valve. The obtained porcine aortic valve was rinsed by shaking at 100 rpm in a normal saline solution containing 20% (v/v) of ethanol (Sinopharm Chemical Reagent Co., Ltd) at 20° C. for 3-5 times, 3-5 minutes each time. After that, the porcine aortic valve was immersed at 20° C. for 3 hours in pure (100%) glycerol (Sinopharm Chemical Reagent Co., Ltd) that was held in a blue-cover reagent bottle completely wrapped with tin foil. Then the porcine aortic valve was immersed successively in each of 50%, 60%, 70%, 75%, 80% and 85% (w/w) aqueous fructose solutions at 4° C. for 30 minutes, each of which was held in a blue-cover reagent bottle completely wrapped with tin foil. Subsequently, the porcine aortic valve was taken out and dried on fibrous desiccant lamination in a dry and clean environment. Finally, the dry porcine aortic valve was hermetically packaged and sterilized with EO in a dry environment containing nitrogen. The prepared dry porcine aortic valve had a water content of 15.7±2.1%, a rehydration time of 4.85±0.78 minutes, a shrinkage temperature of 85.59±2.46° C., a Class I cytotoxicity and a maximum tensile strength of 11.9±4.3 N.

Example 3

Porcine small intestinal submucosa was harvested from an abattoir, subjected to separation, trimming and cleaning, then cross-linked with a 0.625% (v/v) glutaraldehyde solution for more than three days to obtain glutaraldehyde cross-linked porcine small intestinal submucosa. The obtained porcine small intestinal submucosa was cut into small pieces (30 mm×50 mm) which were then rinsed by shaking at 100 rpm in a normal saline solution containing 10% (v/v) of isopropanol at 25° C. for 3-5 times, 3-5 minutes each time. After that, the porcine small intestinal submucosa pieces were immersed at 20° C. for 2 hours in an alcoholic solution containing 50% (v/v) of 1,2,6-hexanetriol (Shanghai Jingchun Biochemical Technology Co., Ltd.), 30% (v/v) of ethanol and 20% (v/v) of polyethylene glycol 400 (Shanghai Jingchun Biochemical Technology Co., Ltd.) that was held in a blue-cover reagent bottle completely wrapped with tin foil. Then the porcine small intestinal submucosa pieces were immersed successively in each of 30%, 40%, 50%, 55%, 60% and 65% (w/v) aqueous saccharose solutions at 20° C. for 20 minutes, each of which was held in a blue-cover reagent bottle completely wrapped with tin foil. Subsequently, in a dry and clean environment, the porcine small intestinal submucosa pieces were taken out and dried on fibrous desiccant lamination. Finally, in a dry and clean environment, the dry porcine small intestinal submucosa pieces were hermetically packaged in dialysis bags and sterilized with EO. The prepared dry porcine small intestinal submucosa had a water content of 16.5±1.6%, a rehydration time of 4.73±0.91 minutes, a shrinkage temperature of 87.34±1.15° C., a Class I cytotoxicity and a maximum tensile strength of 12.7±5.2 N.

Example 4

Porcine pericardium was harvested from an abattoir, subjected to fat separation, trimming and cleaning, then cross-linked with a 0.625% (v/v) glutaraldehyde solution for more than three days. The cross-linked pericardium was cut into small pieces (30 mm×50 mm) which were then rinsed by shaking at 100 rpm in a normal saline solution containing 15% (v/v) of isopropanol at 20° C. for 3-5 times, 3-5 minutes each time. After that, the porcine pericardium pieces were immersed first at 20° C. for 3 hours in an alcoholic solution containing 75% of glycerol and 25% of isopropanol that was held in a blue-cover reagent bottle completely wrapped with tin foil. Then the porcine pericardium pieces were immersed successively in each of 30%, 40%, 50%, 55%, 60% and 65% (w/v) aqueous saccharose solutions at 20° C. for 10 minutes, each of which was held in a blue-cover reagent bottle completely wrapped with tin foil. Subsequently, in a dry and clean environment, the porcine pericardium pieces were taken out and dried on fibrous desiccant lamination. Finally, in a dry and clean environment, the dry porcine pericardium pieces were hermetically packaged in bottles and sterilized by electron beam irradiation. The prepared dry porcine pericardium had a water content of 18.0±1.2%, a rehydration time of 5.15±0.36 minutes, a shrinkage temperature of 87.84±1.66° C., a Class I cytotoxicity and a maximum tensile strength of 14.2±5.8 N.

While the present invention has been disclosed above with reference to several preferred embodiments, these embodiments are not intended to limit the invention in any sense. Those skilled in the art can make changes and modifications without departing from the spirit and scope of the present invention. Therefore, the scope of the invention is intended to be defined by the appended claims.

What is claimed is:

1. A preparation method of a dry animal-derived collagen fiber tissue material, comprising:
   1) rinsing an animal-derived collagen fiber tissue material that has been treated with a crosslinking agent;
   2) immersing the rinsed tissue material in a non-aqueous alcoholic solution for dehydration;
   3) successively immersing the tissue material that has been dehydrated with the non-aqueous alcoholic solution in saccharide solutions of different gradients of concentrations for gradient dehydration;
   4) taking out and drying of the gradient dehydrated tissue material; and
   5) hermetic packaging of the dried tissue material and sterilizing the dried tissue material.

2. The preparation method of claim 1, wherein the biological tissue material is pericardium, heart valves, peritoneum, pleura, small intestinal submucosa, dura mater, spinal dura, ligaments or skin.

3. The preparation method of claim 1, wherein the cross-linking agent in step 1) is one or more of glutaraldehyde, genipin, procyanidins and carbodiimide.

4. The preparation method of claim 1, wherein the rinsing in step 1) is accomplished by shaking at 50-150 rpm for 3-60 minutes at 4-25° C. in a isotonic solution containing 5%-30% (v/v) of isopropanol and/or ethanol.

5. The preparation method of claim 4, wherein the isotonic solution is a normal saline solution, or a phosphate buffer solution having a pH of 6.8-8.6, or a D-Hanks buffer solution having a pH of 6.8-8.6.

6. The preparation method of claim 1, wherein the non-aqueous alcoholic solution in step 2) is a solution of aliphatic alcohol(s) with each aliphatic alcohol having a molecular weight of less than 1000D.

7. The preparation method of claim 6, wherein the non-aqueous alcoholic solution is a solution of a polyether diol and/or a C2-C6 aliphatic alcohol.

8. The preparation method of claim 7, wherein the non-aqueous alcoholic solution contains polyethylene glycol or glycerol accounting for 20%-90% by volume or contains polyethylene glycol and glycerol together accounting for 20%-90% by volume.

9. The preparation method of claim 6, wherein the non-aqueous alcoholic solution is a solution of one or more of polyethylene glycol, triethylene glycol, 1,2,6-hexanetriol, 1,2,4-butanetriol, 1,3-butanediol, 1,4-butanediol, 1,5-pentanediol, glycerol, isopropanol and ethanol.

10. The preparation method of claim 9, wherein the polyethylene glycol has a number-average molecular weight of 200-1000.

11. The preparation method of claim 1, wherein in step 2), the rinsed tissue material is immersed for 30 minutes to 24 hours in a dark condition at 20-37° C.

12. The preparation method of claim 1, wherein each of the saccharide solutions in step 3) is a solution of a moisturizing monosaccharide, disaccharide, trisaccharide, polysaccharide or sugar alcohol that can absorb moisture.

13. The preparation method of claim 12, wherein each of the saccharide solutions is a solution of fructose, saccharose, trehalose, non-crystalline raffinose, chitosan, a chitosan-modified polysaccharide, sorbitol or mannitol.

14. The preparation method of claim 1, wherein the gradient dehydration in step 3) is accomplished by immersing the tissue material that has been dehydrated with the non-aqueous alcoholic solution successively in each of the saccharide solutions of different gradients of concentrations at 4-37° C. in a dark condition for 5 minutes to 48 hours.

15. The preparation method of claim 1, wherein the saccharide solutions of different gradients of concentrations in step 3) are respectively 30%, 40%, 50%, 55%, 60% and 65% (w/v) aqueous saccharose solutions or 50%, 60%, 70%, 75%, 80% and 85% (w/v) aqueous solutions of fructose, trehalose, non-crystalline raffinose, chitosan, chitosan-modified polysaccharide, sorbitol or mannitol.

16. The preparation method of claim 1, wherein in step 4), the gradient dehydrated tissue material is taken out and dried by using a fibrous desiccant or by placing the gradient dehydrated tissue material in a dark condition at 20° C.-37° C. for 10 minutes to 24 hours.

17. The preparation method of claim 16, wherein the fibrous desiccant is selected from the group consisting of raw sheets, folded sheets, sheets in bags, columns and lamination.

18. The preparation method of claim 1, wherein the hermetic packaging is accomplished by hermetically sealing the dried tissue material in a packaging container in an environment with a relative humidity of less than 30% or in an inert environment.

* * * * *